United States Patent
Rudnic

(10) Patent No.: US 7,122,204 B2
(45) Date of Patent: *Oct. 17, 2006

(54) ANTIBIOTIC COMPOSITION WITH INHIBITOR

(75) Inventor: Edward M. Rudnic, N. Potomac, MD (US)

(73) Assignee: Advancis Pharmaceutical Corporation, Germantown, MD (US)

( * ) Notice: Subject to any disclaimer, the term of this patent is extended or adjusted under 35 U.S.C. 154(b) by 381 days.

This patent is subject to a terminal disclaimer.

(21) Appl. No.: 10/419,357

(22) Filed: Apr. 21, 2003

(65) Prior Publication Data

US 2003/0235615 A1    Dec. 25, 2003

Related U.S. Application Data

(63) Continuation of application No. 09/791,536, filed on Feb. 23, 2001, now Pat. No. 6,565,882.

(60) Provisional application No. 60/184,582, filed on Feb. 24, 2000.

(51) Int. Cl.
    A61K 9/22    (2006.01)
    A61K 9/20    (2006.01)

(52) U.S. Cl. .................. 424/468; 424/464; 424/465

(58) Field of Classification Search .............. 424/472, 424/464, 474, 484, 489, 490, 465, 468
See application file for complete search history.

(56) References Cited

U.S. PATENT DOCUMENTS

| | | | | |
|---|---|---|---|---|
| 3,108,046 A | 10/1963 | Harbit | | 167/82 |
| 3,870,790 A | 3/1975 | Lowey et al. | | 424/19 |
| 4,007,174 A | 2/1977 | Laundon | | 260/243 |
| 4,008,246 A | 2/1977 | Ochiai et al. | | 260/306.8 |
| 4,018,918 A | 4/1977 | Ayer et al. | | 514/24 |
| 4,048,306 A | 9/1977 | Maier et al. | | 424/180 |
| 4,226,849 A | 10/1980 | Schor | | 424/19 |
| 4,236,211 A | 11/1980 | Arvesen | | 435/32 |
| 4,250,166 A | 2/1981 | Maekawa et al. | | 424/81 |
| 4,331,803 A | 5/1982 | Watanabe et al. | | 536/7.2 |
| 4,362,731 A | 12/1982 | Hill | | 424/256 |
| 4,369,172 A | 1/1983 | Schor et al. | | 424/19 |
| 4,399,151 A | 8/1983 | Sjoerdsma et al. | | 514/564 |
| 4,430,495 A | 2/1984 | Patt et al. | | 536/16.3 |
| 4,435,173 A | 3/1984 | Siposs et al. | | 609/155 |
| 4,474,768 A | 10/1984 | Bright | | 424/180 |
| 4,517,359 A | 5/1985 | Kobrehel et al. | | 536/7.4 |
| 4,525,352 A | 6/1985 | Cole et al. | | 424/114 |
| 4,529,720 A | 7/1985 | Cole et al. | | 514/191 |
| 4,560,552 A | 12/1985 | Cole et al. | | 424/114 |
| 4,568,741 A | 2/1986 | Livingston | | 536/16.5 |
| 4,598,045 A | 7/1986 | Masover et al. | | 435/34 |
| 4,616,008 A | 10/1986 | Hirai et al. | | 514/200 |
| 4,634,697 A | 1/1987 | Hamashima | | 514/202 |
| 4,644,031 A | 2/1987 | Lehmann et al. | | 524/501 |
| 4,670,549 A | 6/1987 | Morimoto et al. | | 536/7.4 |
| 4,672,109 A | 6/1987 | Watanabe et al. | | 536/7.2 |
| 4,680,386 A | 7/1987 | Morimoto et al. | | 536/7.4 |
| 4,710,565 A | 12/1987 | Livingston et al. | | 536/16.5 |
| 4,723,958 A | 2/1988 | Pope et al. | | 604/890.1 |
| 4,728,512 A | 3/1988 | Mehta et al. | | 424/458 |
| 4,755,385 A | 7/1988 | Etienne et al. | | 424/154 |
| 4,775,751 A | 10/1988 | McShane | | 540/230 |
| 4,794,001 A | 12/1988 | Mehta et al. | | 424/458 |
| 4,808,411 A | 2/1989 | Lu et al. | | 424/441 |
| 4,812,561 A | 3/1989 | Hamashima et al. | | 540/222 |
| 4,828,836 A | 5/1989 | Elger et al. | | 424/419 |
| 4,831,025 A | 5/1989 | Godtfredsen et al. | | 514/195 |
| 4,835,140 A | 5/1989 | Smith et al. | | 514/24 |
| 4,842,866 A | 6/1989 | Horder et al. | | 424/468 |
| 4,849,515 A | 7/1989 | Matier et al. | | 536/16.5 |
| 4,879,135 A | 11/1989 | Greco et al. | | 623/1.48 |
| 4,894,119 A | 1/1990 | Baron, Jr. et al. | | 162/168.2 |
| 4,895,934 A | 1/1990 | Matier et al. | | 536/16.5 |
| 4,904,476 A | 2/1990 | Mehta et al. | | 424/456 |
| 4,915,953 A | 4/1990 | Jordan et al. | | 424/473 |
| 4,945,080 A | 7/1990 | Lindstrom et al. | | 514/29 |
| 4,945,405 A | 7/1990 | Hirota | | 358/516 |
| 4,971,805 A | 11/1990 | Kitanishi et al. | | 424/494 |
| 4,990,602 A | 2/1991 | Morimoto et al. | | 536/7.4 |
| 5,011,692 A | 4/1991 | Fujioka et al. | | 424/426 |
| 5,045,533 A | 9/1991 | Philippe et al. | | 514/29 |
| 5,051,262 A | 9/1991 | Panoz et al. | | 424/468 |
| 5,110,597 A | 5/1992 | Wong et al. | | 424/438 |
| 5,110,598 A | 5/1992 | Kwan et al. | | 424/438 |
| 5,143,661 A | 9/1992 | Lawter et al. | | 264/4.3 |

(Continued)

FOREIGN PATENT DOCUMENTS

EP    0052075    11/1981

(Continued)

OTHER PUBLICATIONS

Erah et al.; The Stability of amoxycillin, clarithromycin and metronidazole in gastric juice: relevance to the treatment of *Helibacter pylori* infection.; Jan. 1997; Journal of Antimicrob. Chemother. 39(1):5-12, PMID: 9044021.

(Continued)

*Primary Examiner*—Humera N Sheikh
(74) *Attorney, Agent, or Firm*—Elliot M. Olstein; Raymond E. Stauffer

(57) ABSTRACT

Antibiotic composition having four dosage forms with different release profiles providing for initial release of a beta lactam antibiotic followed by release of a beta-lactamase inhibitor, followed by release of the antibiotic followed by release of the inhibitor. In a preferred embodiment, release from the second, third and fourth dosage forms is initiated after the component released from the immediately previous form reaches $C_{max}$.

38 Claims, No Drawings

U.S. PATENT DOCUMENTS

| | | | |
|---|---|---|---|
| 5,158,777 A | 10/1992 | Abramowitz et al. | 424/458 |
| 5,178,874 A | 1/1993 | Kwan et al. | 424/438 |
| 5,182,374 A | 1/1993 | Tobkes et al. | 536/16.5 |
| 5,204,055 A | 4/1993 | Sachs et al. | 419/2 |
| 5,213,808 A | 5/1993 | Bar-Shalom et al. | 424/473 |
| 5,229,131 A | 7/1993 | Amidon et al. | 424/451 |
| 5,230,703 A | 7/1993 | Alon | 604/20 |
| 5,274,085 A | 12/1993 | Amano et al. | 536/7.4 |
| 5,288,503 A | 2/1994 | Wood et al. | 424/497 |
| 5,340,656 A | 8/1994 | Sachs et al. | 428/546 |
| 5,387,380 A | 2/1995 | Cima et al. | 264/69 |
| 5,393,765 A | 2/1995 | Infeld et al. | 514/365 |
| 5,395,626 A | 3/1995 | Kotwal et al. | 424/472 |
| 5,395,628 A | 3/1995 | Noda et al. | 424/490 |
| 5,401,512 A | 3/1995 | Rhodes et al. | 424/458 |
| 5,413,777 A | 5/1995 | Sheth et al. | 424/490 |
| 5,414,014 A | 5/1995 | Schneider et al. | 514/535 |
| 5,430,021 A | 7/1995 | Rudnic et al. | 514/14 |
| 5,445,829 A | 8/1995 | Paradissis et al. | 424/480 |
| 5,457,187 A | 10/1995 | Gmeiner et al. | 536/25.5 |
| 5,462,747 A | 10/1995 | Radebaugh et al. | 424/465 |
| 5,466,446 A | 11/1995 | Stiefel et al. | 424/78.37 |
| 5,472,708 A | 12/1995 | Chen | 424/451 |
| 5,476,854 A | 12/1995 | Young | 514/254 |
| 5,490,962 A | 2/1996 | Cima et al. | 264/22 |
| 5,508,040 A | 4/1996 | Chen | 424/451 |
| 5,518,680 A | 5/1996 | Cima et al. | 264/401 |
| 5,538,954 A | 7/1996 | Koch et al. | 514/53 |
| 5,556,839 A | 9/1996 | Greene et al. | 514/29 |
| 5,567,441 A | 10/1996 | Chen | 424/494 |
| 5,576,022 A | 11/1996 | Yang et al. | 424/472 |
| 5,578,713 A | 11/1996 | McGill, III | 536/18.5 |
| 5,599,557 A | 2/1997 | Johnson et al. | 424/500 |
| 5,607,685 A | 3/1997 | Cimbollek et al. | 424/422 |
| 5,633,006 A | 5/1997 | Catania et al. | 424/441 |
| 5,672,359 A | 9/1997 | Digenis et al. | 424/463 |
| 5,705,190 A | 1/1998 | Broad et al. | 424/465 |
| 5,707,646 A | 1/1998 | Yajima et al. | 424/439 |
| 5,719,132 A | 2/1998 | Lin et al. | 514/50 |
| 5,719,272 A | 2/1998 | Yang et al. | 536/7.4 |
| 5,725,553 A | 3/1998 | Moenning | 606/213 |
| 5,733,886 A | 3/1998 | Baroody et al. | 514/24 |
| 5,756,473 A | 5/1998 | Liu et al. | 514/29 |
| 5,780,446 A | 7/1998 | Ramu | 514/34 |
| 5,808,017 A | 9/1998 | Chang | 536/7.4 |
| 5,827,531 A | 10/1998 | Morrison et al. | 424/450 |
| 5,837,284 A | 11/1998 | Mehta et al. | 424/459 |
| 5,837,829 A | 11/1998 | Ku | 536/7.4 |
| 5,840,329 A | 11/1998 | Bai | 424/458 |
| 5,844,105 A | 12/1998 | Liu et al. | 536/18.5 |
| 5,849,776 A | 12/1998 | Czernielewski et al. | 514/398 |
| 5,852,180 A | 12/1998 | Patel | 536/7.4 |
| 5,858,986 A | 1/1999 | Liu et al. | 514/29 |
| 5,864,023 A | 1/1999 | Ku et al. | 536/7.2 |
| 5,869,170 A | 2/1999 | Cima et al. | 428/304.4 |
| 5,872,104 A | 2/1999 | Vermeulen et al. | 514/29 |
| 5,872,229 A | 2/1999 | Liu et al. | 536/18.6 |
| 5,877,243 A | 3/1999 | Sarangapani | 524/139 |
| 5,883,079 A | 3/1999 | Zopf et al. | 514/25 |
| 5,892,008 A | 4/1999 | Ku et al. | 536/18.5 |
| 5,910,322 A | 6/1999 | Rivett et al. | 424/484 |
| 5,919,219 A | 7/1999 | Knowlton | 607/102 |
| 5,919,489 A | 7/1999 | Saleki-Gerhardt et al. | 424/501 |
| 5,919,916 A | 7/1999 | Gracey et al. | 536/7.2 |
| 5,929,219 A | 7/1999 | Hill | 536/7.2 |
| 5,932,710 A | 8/1999 | Liu et al. | 536/18.7 |
| 5,945,124 A | 8/1999 | Sachs et al. | 424/472 |
| 5,945,405 A | 8/1999 | Spanton et al. | 514/29 |
| 5,972,373 A | 10/1999 | Yajima et al. | 424/439 |
| 5,980,942 A | 11/1999 | Katzhendler et al. | 424/465 |
| 5,998,194 A | 12/1999 | Summers, Jr. et al. | 435/252.33 |
| 6,010,718 A | 1/2000 | Al-Razzak et al. | 424/464 |
| 6,027,748 A | 2/2000 | Conte et al. | 424/458 |
| 6,031,093 A | 2/2000 | Cole et al. | 540/349 |
| 6,048,977 A | 4/2000 | Cole et al. | 540/349 |
| 6,051,255 A | 4/2000 | Conley et al. | 424/482 |
| 6,051,703 A | 4/2000 | Cole et al. | 514/210.06 |
| 6,059,816 A | 5/2000 | Moenning | 606/213 |
| 6,063,917 A | 5/2000 | Ascher et al. | 540/217 |
| 6,068,859 A | 5/2000 | Curatolo et al. | 424/490 |
| 6,117,843 A | 9/2000 | Baroody et al. | 514/24 |
| 6,120,803 A | 9/2000 | Wong et al. | 424/473 |
| 6,127,349 A | 10/2000 | Chasalow | 514/77 |
| 6,132,768 A | 10/2000 | Sachs et al. | 424/458 |
| 6,132,771 A | 10/2000 | Depui et al. | 424/468 |
| 6,159,491 A | 12/2000 | Durrani | 424/430 |
| 6,183,778 B1 | 2/2001 | Conte et al. | 424/472 |
| 6,214,359 B1 | 4/2001 | Bax | 424/400 |
| 6,218,380 B1 | 4/2001 | Cole et al. | 514/210.06 |
| 6,228,398 B1 | 5/2001 | Devane et al. | 424/484 |
| 6,231,875 B1 | 5/2001 | Sun et al. | 424/401 |
| 6,248,363 B1 | 6/2001 | Patel et al. | 424/497 |
| 6,270,805 B1 | 8/2001 | Chen et al. | 424/497 |
| 6,280,771 B1 | 8/2001 | Monkhouse et al. | 424/484 |
| 6,294,199 B1 | 9/2001 | Conley et al. | 424/468 |
| 6,296,873 B1 | 10/2001 | Katzhendler et al. | 424/465 |
| 6,299,903 B1 | 10/2001 | Rivett et al. | 424/464 |
| 6,306,436 B1 | 10/2001 | Chungi et al. | 424/464 |
| 6,309,663 B1 | 10/2001 | Patel et al. | 424/450 |
| 6,322,819 B1 | 11/2001 | Burnside et al. | 424/494 |
| 6,333,050 B1 | 12/2001 | Wong et al. | 424/473 |
| 6,340,475 B1 | 1/2002 | Shell et al. | 424/469 |
| 6,352,720 B1 | 3/2002 | Martin et al. | 424/464 |
| 6,358,525 B1 | 3/2002 | Guo et al. | 424/464 |
| 6,358,528 B1 | 3/2002 | Grimmett et al. | 424/474 |
| 6,384,081 B1 | 5/2002 | Berman | 514/621 |
| 6,399,086 B1 | 6/2002 | Katzhendler et al. | 424/405 |
| 6,403,569 B1 | 6/2002 | Achterrath | 514/50 |
| 6,406,717 B1 | 6/2002 | Cherukuri | 424/484 |
| 6,440,462 B1 | 8/2002 | Raneburger et al. | 424/489 |
| 6,444,796 B1 | 9/2002 | Suh et al. | 536/7.2 |
| 6,468,964 B1 | 10/2002 | Rowe | 514/6 |
| 6,479,496 B1 | 11/2002 | Wolff | 514/252.17 |
| 6,495,157 B1 | 12/2002 | Pena et al. | 424/433 |
| 6,497,901 B1 | 12/2002 | Royer | 424/468 |
| 6,506,886 B1 | 1/2003 | Lee et al. | 536/7.2 |
| 6,514,518 B1 | 2/2003 | Monkhouse et al. | 424/427 |
| 6,515,010 B1 | 2/2003 | Franchini et al. | 514/411 |
| 6,515,116 B1 | 2/2003 | Suh et al. | 536/7.2 |
| 6,530,958 B1 | 3/2003 | Cima et al. | 623/23.51 |
| 6,541,014 B1 | 4/2003 | Rudnic et al. | 424/400 |
| 6,544,555 B1 | 4/2003 | Rudnic et al. | 424/468 |
| 6,548,084 B1 | 4/2003 | Leonard et al. | 424/482 |
| 6,550,955 B1 | 4/2003 | D'Silva | 366/130 |
| 6,551,584 B1 | 4/2003 | Bandyopadhyay et al. | 424/78.04 |
| 6,551,616 B1 | 4/2003 | Notario et al. | 424/464 |
| 6,558,699 B1 | 5/2003 | Venkatesh | 424/464 |
| 6,565,873 B1 | 5/2003 | Shefer et al. | 424/426 |
| 6,565,882 B1 | 5/2003 | Rudnic | 424/472 |
| 6,569,463 B1 | 5/2003 | Patel et al. | 424/497 |
| 6,585,997 B1 | 7/2003 | Moro et al. | 424/434 |
| 6,599,884 B1 | 7/2003 | Avrutov et al. | 514/29 |
| 6,605,069 B1 | 8/2003 | Albers et al. | 604/264 |
| 6,605,300 B1 | 8/2003 | Burnside et al. | 424/452 |
| 6,605,751 B1 | 8/2003 | Gibbins et al. | 602/41 |
| 6,610,323 B1 | 8/2003 | Lundberg et al. | 424/458 |
| 6,610,328 B1 | 8/2003 | Rudnic et al. | 424/468 |
| 6,617,436 B1 | 9/2003 | Avrutov et al. | 536/7.2 |
| 6,623,757 B1 | 9/2003 | Rudnic et al. | 424/468 |
| 6,623,758 B1 | 9/2003 | Rudnic et al. | 424/468 |
| 6,624,292 B1 | 9/2003 | Lifshitz et al. | 536/7.2 |
| 6,627,222 B1 | 9/2003 | Rudnic et al. | 424/468 |
| 6,627,743 B1 | 9/2003 | Liu et al. | 536/7.2 |

| Patent No. | Date | Inventor | Class |
|---|---|---|---|
| 6,630,498 B1 | 10/2003 | Gudipati et al. | 514/397 |
| 6,632,453 B1 | 10/2003 | Rudnic et al. | 424/468 |
| 6,635,280 B1 | 10/2003 | Shell et al. | 424/469 |
| 6,638,532 B1 | 10/2003 | Rudnic et al. | 424/468 |
| 6,642,276 B1 | 11/2003 | Wadhwa | 514/781 |
| 6,663,890 B1 | 12/2003 | Rudnic et al. | 424/468 |
| 6,663,891 B1 | 12/2003 | Rudnic et al. | 424/468 |
| 6,667,042 B1 | 12/2003 | Rudnic et al. | 424/400 |
| 6,667,057 B1 | 12/2003 | Rudnic et al. | 424/468 |
| 6,669,948 B1 | 12/2003 | Rudnic et al. | 424/400 |
| 6,669,955 B1 | 12/2003 | Chungi et al. | 424/464 |
| 6,673,369 B1 | 1/2004 | Rampal et al. | 424/468 |
| 6,682,759 B1 | 1/2004 | Lim et al. | 424/468 |
| 6,696,426 B1 | 2/2004 | Singh et al. | 514/58 |
| 6,702,803 B1 | 3/2004 | Kupperblatt et al. | 604/890.1 |
| 6,706,273 B1 | 3/2004 | Roessler | 424/422 |
| 6,723,340 B1 | 4/2004 | Gusler et al. | 424/468 |
| 6,723,341 B1 | 4/2004 | Rudnic et al. | 424/468 |
| 6,730,320 B1 | 5/2004 | Rudnic et al. | 424/468 |
| 6,730,325 B1 | 5/2004 | Devane et al. | 424/489 |
| 6,735,470 B1 | 5/2004 | Henley et al. | 604/20 |
| 6,740,664 B1 | 5/2004 | Cagle et al. | 514/311 |
| 6,746,692 B1 | 6/2004 | Conley et al. | 424/468 |
| 6,756,057 B1 | 6/2004 | Storm et al. | 424/472 |
| 6,767,899 B1 | 7/2004 | Kay et al. | 514/62 |
| 6,777,420 B1 | 8/2004 | Zhi et al. | 514/272 |
| 6,783,773 B1 | 8/2004 | Storm et al. | 424/468 |
| 6,824,792 B1 | 11/2004 | Foreman et al. | 424/487 |
| 6,872,407 B1 | 3/2005 | Notario et al. | 424/464 |
| 6,878,387 B1 | 4/2005 | Petereit et al. | 424/490 |
| 6,929,804 B1 | 8/2005 | Rudnic et al. | 424/468 |
| 6,984,401 B1 | 1/2006 | Rudnic et al. | 424/489 |
| 6,991,807 B1 | 1/2006 | Rudnic et al. | 424/468 |
| 2001/0046984 A1 | 11/2001 | Rudnic et al. | 514/210.09 |
| 2001/0048944 A1 | 12/2001 | Rudnic et al. | 424/468 |
| 2002/0004070 A1 | 1/2002 | Rudnic et al. | 424/468 |
| 2002/0004499 A1 | 1/2002 | Rudnic et al. | 514/192 |
| 2002/0015728 A1 | 2/2002 | Payumo et al. | 424/451 |
| 2002/0028920 A1 | 3/2002 | Lifshitz et al. | 536/7.1 |
| 2002/0042394 A1 | 4/2002 | Hogenkamp et al. | 514/53 |
| 2002/0068078 A1 | 6/2002 | Rudnic et al. | 424/408 |
| 2002/0068085 A1 | 6/2002 | Rudnic et al. | 424/468 |
| 2002/0081332 A1 | 6/2002 | Rampal et al. | 424/461 |
| 2002/0103261 A1 | 8/2002 | Ninkov | 514/731 |
| 2002/0106412 A1 | 8/2002 | Rowe et al. | 424/490 |
| 2002/0115624 A1 | 8/2002 | Behar et al. | 514/42 |
| 2002/0119168 A1 | 8/2002 | Rudnic et al. | 424/400 |
| 2002/0136764 A1 | 9/2002 | Rudnic et al. | 424/457 |
| 2002/0136765 A1 | 9/2002 | Rudnic et al. | 424/457 |
| 2002/0136766 A1 | 9/2002 | Rudnic et al. | 424/457 |
| 2002/0150619 A1 | 10/2002 | Rudnic et al. | 424/468 |
| 2002/0197314 A1 | 12/2002 | Rudnic et al. | 424/468 |
| 2003/0012814 A1 | 1/2003 | Rudnic et al. | 424/468 |
| 2003/0018295 A1 | 1/2003 | Henley et al. | 604/20 |
| 2003/0049311 A1 | 3/2003 | McAllister et al. | 424/452 |
| 2003/0064100 A1 | 4/2003 | Rudnic et al. | 424/468 |
| 2003/0073647 A1 | 4/2003 | Chao et al. | 514/42 |
| 2003/0073648 A1 | 4/2003 | Chao et al. | 514/42 |
| 2003/0073826 A1 | 4/2003 | Chao et al. | 536/18.7 |
| 2003/0077323 A1 | 4/2003 | Rudnic et al. | 424/468 |
| 2003/0086969 A1 | 5/2003 | Rudnic et al. | 424/486 |
| 2003/0091627 A1 | 5/2003 | Sharma | 424/465 |
| 2003/0096006 A1 | 5/2003 | Rudnic et al. | 424/468 |
| 2003/0096007 A1 | 5/2003 | Rudnic et al. | 424/468 |
| 2003/0096008 A1 | 5/2003 | Rudnic et al. | 424/468 |
| 2003/0099706 A1 | 5/2003 | Rudnic et al. | 424/468 |
| 2003/0099707 A1 | 5/2003 | Rudnic et al. | 424/468 |
| 2003/0104054 A1 | 6/2003 | Rudnic et al. | 424/468 |
| 2003/0104055 A1 | 6/2003 | Rudnic et al. | 424/468 |
| 2003/0104056 A1 | 6/2003 | Rudnic et al. | 424/468 |
| 2003/0104058 A1 | 6/2003 | Rudnic et al. | 424/468 |
| 2003/0124196 A1 | 7/2003 | Weinbach et al. | 424/499 |
| 2003/0129236 A1 | 7/2003 | Heimlich et al. | 424/470 |
| 2003/0143268 A1 | 7/2003 | Pryce Lewis et al. | 424/464 |
| 2003/0147953 A1 | 8/2003 | Rudnic et al. | 424/468 |
| 2003/0190360 A1 | 10/2003 | Baichwal et al. | 424/470 |
| 2003/0198677 A1 | 10/2003 | Pryce Lewis et al. | 424/471 |
| 2003/0199808 A1 | 10/2003 | Henley et al. | 604/20 |
| 2003/0203023 A1 | 10/2003 | Rudnic et al. | 424/468 |
| 2003/0206951 A1 | 11/2003 | Rudnic et al. | 424/468 |
| 2003/0216555 A1 | 11/2003 | Lifshitz et al. | 536/7.1 |
| 2003/0216556 A1 | 11/2003 | Avrutov et al. | 536/7.2 |
| 2003/0232089 A1 | 12/2003 | Singh et al. | 424/488 |
| 2003/0235615 A1 | 12/2003 | Rudnic | 424/468 |
| 2004/0018234 A1 | 1/2004 | Rudnic et al. | 424/468 |
| 2004/0033262 A1 | 2/2004 | Kshirsagar et al. | 424/468 |
| 2004/0043073 A1 | 3/2004 | Chen et al. | 424/486 |
| 2004/0047906 A1 | 3/2004 | Percel et al. | 424/468 |
| 2004/0048814 A1 | 3/2004 | Vanderbist et al. | 514/29 |
| 2004/0052842 A1 | 3/2004 | Rudnic et al. | 424/468 |
| 2004/0058879 A1 | 3/2004 | Avrutov et al. | 514/29 |
| 2004/0091528 A1 | 5/2004 | Rogers et al. | 424/468 |
| 2004/0126427 A1 | 7/2004 | Venkatesh et al. | 424/469 |
| 2004/0176737 A1 | 9/2004 | Henley et al. | 604/501 |
| 2004/0219223 A1 | 11/2004 | Kunz | 424/489 |
| 2004/0253249 A1 | 12/2004 | Rudnic et al. | 424/184.1 |
| 2004/0265379 A1 | 12/2004 | Conley et al. | 424/465 |
| 2005/0053658 A1 | 3/2005 | Venkatesh et al. | 424/468 |
| 2005/0064033 A1 | 3/2005 | Notario et al. | 424/468 |
| 2005/0064034 A1 | 3/2005 | Li et al. | 424/469 |
| 2005/0163857 A1 | 7/2005 | Rampal et al. | 424/489 |
| 2005/0238714 A1 | 10/2005 | Rudnic et al. | 424/468 |

FOREIGN PATENT DOCUMENTS

| | | |
|---|---|---|
| EP | 0293885 | 12/1988 |
| EP | 0436370 | 7/1991 |
| EP | 0652008 A1 | 5/1995 |
| FR | 2585948 | 2/1982 |
| GB | 2087235 | 5/1982 |
| WO | WO 90/08537 | 8/1990 |
| WO | WO 94/27557 | 12/1994 |
| WO | WO 95/20946 | 8/1995 |
| WO | WO 95/30422 | 11/1995 |
| WO | WO 96/04908 | 2/1996 |
| WO | WO 97/22335 | 6/1997 |
| WO | WO 98/22091 | 5/1998 |
| WO | WO 98/46239 | 10/1998 |
| WO | WO 99/03453 | 1/1999 |
| WO | WO 99/40097 | 8/1999 |
| WO | WO 00/48607 | 8/2000 |
| WO | WO 00/61116 | 10/2000 |
| WO | WO 01/26663 | 4/2001 |
| WO | WO 02/38577 | 5/2002 |
| WO | WO 03/029439 | 4/2003 |

OTHER PUBLICATIONS

Yousef et al.: Combined action of amoxycillin and dicloxicillin against *Staphylococcus aureus* in vitro; Sep. 1985; Pharmazie; 40(9):650-1 PMID: 3877939.

Gnarpe et al; Pencillin combinations against multi-resistant urinary pathogens as an alternative to gentamycin treatment; 1976; Microbios.; 16(65-66):201-6 PMID: 18651.

Adjei et al., Comparative Pharmacokinetic Study of Continuous Venous Infusion Fluorouracil and Oral Fluorouracil With Eniluracil in Patients with Advanced Solid Tumors, Journal of Clinical Oncology, vol. 20, Issue 6 (Mar.), 2002, 1686-1691.

Andes, Pharmacokinetics and Pharmacodynamic Properties of Antimicrobials in the Therapy of Respiratory Tract Infections, Current Opinion in Infectious Diseases, 14(2):165-172, Apr. 2001. (Abstract).

Auckenthaler, Pharmacokinetics and Pharmacodynamics of Oral Beta-Lactam Antibiotics as a Two-Dimensional Approach to Their Efficacy, J Antimicrob Chemother, (2002) 50, 13-17.

Berry et al., Bacteriological Efficacies of Three Macrolides Compared with Those Amoxicilin-Clavulanate Against Streptococcus Pneumoniae and Haemophilus Influenzae, Antimicrob Agents Chemother. Dec. 1998; 42(12):3193-3199.

Bhargava et al., Pulsed Feeding During Fed-Batch Fungal Fermentation Leads to Reduced Viscosity Without Detrimentally Affecting Protein Expression, Biotechnology and Bioengineering, vol. 81, No. 3, Feb. 5, 2003, pp. 341-347.

Bhargava et al., Pulsed Feeding During Fed-Batch Aspergillus Oryzae Fermentation Leads to Improved Oxygen Mass Transfer, Biotechnol. Prog. 2003, 19, 1091-1094.

Bhargava et al., Pulsed Addition of Limiting-Carbon During Aspergillus Oryzae Fermentation Leads to Improved Productivity of a Recombinant Enzyme, Biotechnology and Bioengineering, vol. 82, No. 1, Apr. 5, 2003, pp. 111-117.

Bishai, Comparative Effectiveness of Different Macrolides: Clarithromycin, Azithromycin, and Erythromycin, Johns Hopkins Point of Care Information Technology (POC-IT), 2000.

Bradley, Staphylococcus Aureus Pneumonia: Emergence of MRSA in the Community, Semin Respir Crit Care Med. 2005; 26 (6): 643-649.

Brogden et al., Cefixime. A Review of Its Antibacterial Activity. Pharmacokinetic Properties and Therapeutic Potential, Drugs, Oct. 1989; 38 (4): 524-50. (Abstract).

Burgess et al., A Time-Kill Evaluation of Clarithromycin and Azithromycin Against Two Extracellular Pathogens and the Development of Resistance, The Annals of Pharmacotherapy: vol. 33, No. 12, pp. 1262-1265. (Abstract), 1999.

Byfield et al., Relevance of the Pharmacology of Oral Tegafur to its Use as a 5-FU Pro-Drug., Cancer Treat Rep. Jun. 1985; 69 (6): 645-52. (Abstract).

Cappelletty et al., Bactericidal Activities of Cefprozil, Penicillin, Cefactor, Cefixime, and Loracarbef against Penicillin-Susceptible and -Resistant Streptooccus Pneumoniae in an In Vitro Pharmacodynamic Infection Model, Antimicrobial Agents and Chemotherapy, May 1996, p. 1148-1152.

Cha et al., Pulsatile Delivery of Amoxicillin Against Streptococcus Pneumoniae, Journal of Antimicrobial Chemotherapy, Advance Access Published Oct. 14, 2004.

Craig, Antibiotic Selection Factors and Description of a Hospital-Based Outpatient Antibiotic Therapy Program in the USA, Eur J Clin Microbiol Infect Dis. Jul. 1995;14(7):636-42. (Abstract).

Cremieux et al., Ceftriaxone Diffusion into Cardiac Fibrin Vegetation. Qualitative and Quantitative Evaluation by Autoradiography, Fundam Clin Pharmacol. 1991;5(1):53-60. (Abstract).

Endo et al., Fungicidal Action of Aureobasidin A, a Cyclic Depsipeptide Antifungal Antibiotic, against *Saccharomyces cerevisiae*, Antimicrobial Agents and Chemotherapy, Mar. 1997, p. 672-676.

Feder et al., Once-Daily Therapy for Streptococcal Pharyngitis With Amoxicillin, American Academy of Pediatrics, vol. 103(1), Jan. 1999, pp. 47-51.

Freeman et al., The Cyclosporin-Erythromycin Interaction: Impaired First Pass Metabolism in the Pig, Br J Pharmacol. Jul. 1991;103(3):1709-12. (Abstract).

Frimodt-Moller, Correlation Between Pharmacokinetic / Pharmacodynamic Parameters and Efficacy for Antibiotics in the Treatment of Urinary Tract Infection, Int. J. Antimicrob. Agents, 19 (2002) 546-53.

Furlanut et al., Pharmacokinetic Aspects of Levofloxacin 500mg Once Daily During Sequential Intravenous/Oral Therapy in Patients with Lower Respiratory Tract Infections, Journal of Antimicrobial Chemotherapy (2003) 51, 101-106.

Gill et al., In Vivo Activity and Pharmacokinetic Evaluation of a Novel Long-Acting Carbapenem Antibiotic, MK-826 (L-749, 345), Antimicrobial Agents and Chemotherapy, Aug. 1998;42(8):1996-2001.

Gordon et al., Rationale for Single and High Dose Treatment Regimens with Azithromycin, Pediatric Infectious Disease Journal. 23(2) Supplement: S102-S107, Feb. 2004. (Abstract).

Goswick et al., Activities of Azithromycin and Amphotericin B Against Naegleria Fowleri In Vitro and in a Mouse Model of Primary Amebic Meningoencephalitis, Antimicrob Agents Chemother. Feb. 2003; 47(2): 524-528.

Harbarth et al., Prolonged Antibiotic Prophylaxis After Cardiovascular Surgery and Its Effect on Surgical Site Infections and Antimicrobial Resistance, Circulation Jun. 27, 2000; 101:2916-2921.

Haney, New Drugs Kill Bacteria Resistant to Antibiotics, Called Ketolides, They are Chemically New to the Harmful Bugs, Thursday, Sep. 21, 2000, Seattle Post-Intelligencer.

Harris et al., Esophageal Carcinoma: Curative Treatment, Combined Modalities, The Virtual Hospital, (1992).

Hickey et al., Production of Enterolysin A by a Raw Milk Enterococcal Isolate Exhibiting Multiple Virulence Factors, Microbiology 149 (2003), 655-664.

Hirata et al., Pharmacokinetic Study of S-1, a Novel Oral Fluorouracil Antihumor Drug, Clinical Cancer Research vol. 5, 2000-2005, Aug. 1999.

Hoff et al., Phase I Study with Pharmacokinetics of S-1 on an Oral Daily Schedule for 28 Days in Patients with Solid Tumors, Clinical Cancer Research vol. 9, 134-142, Jan. 2003.

Hoffman et al., Pharmacodynamic and Pharmacokinetic Rationales for the Development of an Oral Controlled-Release Amoxicillin Dosage Form, Journal of Controlled Release 54 (1998) 29-37.

Hoffman et al., Influence of Macrolide Susceptibility on Efficacies of Clarithromycin and Azithromycin Against *Streptococcus pneumoniae* in a Murine Lung Infection Model, Antimicrobial Agents and Chemotherapy, Feb. 2003, p. 739-746, vol. 47, No. 2.

Hyde et al., Macrolide Resistance Among Invasive *Streptococcus pneumoniae* Isolates, JAMA. Oct. 17, 2001; 286(15):1857-62. (Abstract).

Iba et al., Comparison Between Continuous Intravenous and Oral Administration of 5-FU with LV, Gan To Kagaku Ryoho. Apr. 1999; 26(5):631-5 (Abstract).

Kaplan et al., Macrolide Therapy of Group A *Streptococcal pharyngitis*: 10 Days of Macrolide Therapy (Clarithromycin) is More Effective in *Streptococcal eradication* Than 5 Days (Azithromycin), Clin Infect Dis. Jun. 15, 2001;32(12):1798-802. Epub May 21, 2001. (Abstract).

Klugman, Bacteriological Evidence of Antibiotic Failure in Pneumococcal Lower Respiratory Tract Infections, Eur Respir J 2002; 20 Suppl. 36, 3s-8s.

Kramar et al., Statistical Optimisation of Diclofenac Sustained Release Pellets Coated with Polymethacrylic Films, Int J Pharm. Apr. 30, 2003;256(1-2):43-52. (Abstract).

Laine et al., Frequency and Clinical Outcome of Potentially Harmful Drug Metabolic Interactions in Patients Hospitalized on Internal and Pulmonary Medicine Wards: Focus on Warfarin and Cisapride, Therapeutic Drug Monitoring. 22(5):503-509, Oct. 2000. (Abstract).

Laine et al., Frequency and Clinical Outcome of Potentially Harmful Drug Metabolic Interactions in Patients Hospitalized on Internal and Pulmonary Medicine Wards: Focus on Warfarin and Cisapride, Therapeutic Drug Monitoring. 22(5):503-509, 2000.

Lamb et al., Ceftriaxone: An Update of its Use in the Management of Community-Acquired and Noscocomial Infections, Drugs. 2002;62(7):1041-89. (Abstract).

Lemer-Tung et al., Pharmacokinetics of Intrapericardial Administration of 5-Fluorouracil, Cancer Chemother Pharmacol. 1997;40(4):318-20. (Abstract).

Lin et al., Multiple-Dose Pharmacokinetics of Ceftibuten in Healthy Volunteers, Antimicrobial Agents and Chemotherapy, Feb. 1995, p. 356-358.

Lindsey et al., Extraction of Antibiotics From Agricultural Wastewater, USGS, 220th ACS Meeting Washington, D.C.; Aug. 20-24, 2000 (Abstract).

Livermore et al., Activity of Ertapenem Against Neisseria Gonorrhoeae, Journal of Antimicrobial Chemotherapy 2004 54(1):280-281.

Lovmar et al., Kinetics of Macrolide Action, The Josamycin and Erythromycin Cases, J. Biol. Chem., vol. 279, Issue 51, 53506-53515, Dec. 17, 2004.

Mainz et al., Pharmacokinetics of Lansoprazole, Amoxicillin and Clarithromycin After Simultaneous and Single Admistration, Journal of Antimicrobial Chemotherapy (2002) 50, 699-706.

Marten et al., Monthly Report, Jul. 2004, Pulsatile Dosing of Antifungal Compounds, UMBC; to Dr. Robert J. Guttendorf, Advancis Pharmaceutical Corp.

Marten et al., Monthly Report, Aug. 2004, Pulsatile Dosing of Antifungal Compounds, UMBC; to Dr. Robert J. Guttendorf, Advancis Pharmaceutical Corp.

Mazzei et al., How Macrolide Pharmacodynamics Affect Bacterial Killing, Infect Med 16(sE):22-28, 1999. (Abstract).

Nightingale, Pharmacokinetics and Pharmacodynamics of Newer Macrolides, Pediatric Infectious Disease Journal. 16(4):438-443, Apr. 1997. (Abstract).

Olofinlade et al. Anal Carcinoma: A 15-Year Retrospective Analysis, Scand J Gastroenterol 2000:35;1194-1199.

Pacifico et al., Comparative Efficacy and Safety of 3-Day Azithromycin and 10-Day Penicillin V Treatment of Group A Beta-Hemolytic *Streptococcal pharyngitis* in Children, Antimicroial Agents and Chemotherapy, Apr. 1996, 1005-1008, vol. 40, No. 4. (Abstract).

Parmar-Lapasia et al., A Comparison of Two Macrolide Antibiotics in the Treatment of Community-Acquired Infections, P & T (Pharmacy & Therapeutics), Oct. 2003, vol. 28, No. 10.

Peters et al., Fluorouracil (5FU) Pharmacokinetics in 5FU Prodrug Formulations with a Dihydropyrimidine Dehydrogenase Inhibitor, Journal of Clinical Oncology, vol. 19, Issue 22 (Nov. 15, 2001): 4267-4269.

Polak, Pharmacokinetics of Amphotericin B and Flucytosine, Postgrad Med J. Sep. 1979;55(647):667-70. (Abstract).

Porter et al., Antibiotics and Infectious Diseases in Otolaryngology—HNS, Grand Rounds Presentation, UTMB, Dept. of Otolaryngology, May 8, 2002.

Ramminger et al., Transition-Metal Catalyzed Synthesis of Ketoprofen, J. Braz. Chem. Soc. vol. 11, No. 2, 105-111, 2000.

Ramu, Compounds and Methods that Reduce the Risk of Extravasation Injury Associated with the Use of Vesicant Antineoplastic Agents, Baylor College of Medicine, Aug. 6, 1998.

Ranga Rao et al., Influence of Molecular Size and Water Solubility of the Solute on its Release from Swelling and Erosion Controlled Polymeric Matrices, Journal of Controlled Release, 12 (1990) 133-141.

Reza et al., Comparative Evaluation of Plastic, Hydrophobic and Hydrophilic Polymers as Matrices for Controlled-Release Drug Delivery, J. Pharm Pharmaceut Sci, 6(2):282-291, 2003.

Richardson, The Discovery and Profile of Fluconazole, J Chemother. Feb. 1990;2(1):51-4 (Abstract) and Houang et al., Fluconazole Levels in Plasma and Vaginal Secretions of Patients After a 150-Milligram Single Oral Dose and Rate of Eradication of Infection in Vaginal Candidiasis, Antimicrob Agents Chemother. May 1990; 34(5):909-10 (Abstract).

Rivkees et al., Dexamethasone Treatment of Virilizing Congenital Adrenal Hyperplasia: The Ability to Achieve Normal Growth, Pediatrics 2000; 106; 767-773.

Roblin et al., In Vitro Activity of a New Ketolide Antibiotic, HMR 3647, Against Chlamydia Pneumoniae, Antimicrob Agents Chemother. Jun. 1998; 42(6): 1515-1516.

Santini et al., The Potential of Amifostine: From Cytoprotectant to Therapeutic Agent, Haematologica Nov. 1999; 84(ii): 1035-1042.

Sanz et al., Cefepime Plus Amikacin Versus Piperacillin-Tazobactam Plus Amikacin for Initial Antibiotic Therapy in Hematology Patients with Febrile Neutropenia: Results of an Open, Randomized, Multicentre Trial, Journal of Antimicrobial Chemotherapy (2002) 50, 79-88.

Schaad et al., Azithromycin Versus Penicillin V for Treatment of Acute Group A *Streptococcal pharyngitis*, The Pediatric Infectious Disease Journal: vol. 21(4) Apr. 2002, pp. 304-308.

Schweizer et al., "Single Shot" Prevention in Abdominal Surgery. Antibiotics with Long Half-Life (Cefriaxone, Ornidazole) vs. Antibiotics with Short Half-Life (Cefazolin, Metronidazole, Clindamycin), Helv Chir Acta. Apr. 1994;60(4):483-8. (Abstract).

Shvartzman et al., Treatment of *Streptococcal pharyngitis* with Amoxycillin Once A Day, BMJ vol. 306, pp. 1170-1172, May 1, 1993.

Suda et al., The Synthesis and In Vitro and In Vivo Stability of 5-Fluorouracil Prodrugs Which Possess Serum Albumin binding Potency, Biol Pharm Bull. Sep. 1993;16(9):876-8. (Abstract).

Sandip et al., Controlled Release Formulation of Tramadol Hydrochloride Using Hydrophilic and Hydrophobic Matrix System, AAPS PharmSciTech 2003; 4 (3) Article 31.

Todar's Online Textbook of Bacteriology, Antimicrobial Agents Used in Treatment of Infectious Disease, 2002 Kenneth Todar University of Wisconsin-Madison Department of Bacteriology.

Vanderkooi et al., Antimicrobial Resistance and the Pneumococcus, Infectious Diseases and Microbiology, vol. 3, Issue 5, May 2004.

Villalobos et al., Pharmacokinetics and Pharmacodynamics of Antibacterial Agents in Pediatrics: A Practical Approach, Jacksonville Medicine, Aug. 1998.

Waters, Colorectal Cancer-Drug Treatment, Hospital Pharmacist, vol. 11, pp. 179-192, May 2004.

Wattenberg, Prevention of Carcinogenesis of the Respiratory Tract By Chemopreventive Agents Delivered By Aerosol, International Society of Cancer Chemoprevention, vol. 1, No. 5, Jan. 2003.

Whitehead et al., Amoxycillin Release From a Floating Dosage Form Based on Alginates, International Journal of Pharmaceutics 210 (2000) 45-49.

About Macrolides, About That Bug.com, 2006.

Amoxycillin (As Trihydrate), Moxyvit, 2003.

Amoxicillin + Clavulanate, PetPlace.com, 1999.

Answers.com, Macrolide, 2006.

Antimetabolites, GPnotebook, 2005.

Augmentin, Product Information, GlaxoSmithKline, Physicians Desk References, pp. 1421-1433 2004.

Augmentin XR (PDR entry for) (GlaxoSmithKline), (Amoxicillin/Clavulanate Potassium), Extended Release Tablets, Jun. 2004.

Biaxin XL, Once-Daily Biaxin XL Clarithromycin Extended-Release Tablets, Abbott Laboratories Online, 2005.

Biaxin XL, Once-daily, Abbott, 2004.

Citizen Petition, McNeil Consumer & Specialty Pharmaceuticals, Mar. 19, 2004.

Clarithromycin Extended-Release Scientific Posters Presented to the 39th Interscience Conference on Antimicrobial Agents and Chemotherapy (ICAAC), San Francisco, Sep. 26-29, 1999.

Clearance and the Elimination Rate Constant, Ke (Elimination Rate)—Half-Life, Oct. 14, 2002.

Complementary Medicine Saves Money, Medicine, Greenhealthwatch.com, 1998.

Cross-Reference Art Collections, 901-907; USPTO.gov, 2006.

Declaration of Michael J. Rybak. fromthe prosecution history of U.S. Appl. No. 09/762,092; filed Sep. 23, 2002.

Dispensing Errors With Depakote, New Formulation Creates Confusion, Patient Safety, Practitioners Reporting News, USP Issued Mar. 3, 2001.

Drugs.com, Drug Information For Diclofenac (Topical), 2006.

Drug, Bio-Affecting and Body Treating Compositions (Class 424), 475 Sustained or differential release, United States Patent and Trademark Office. (2006).

Elimination Rate Consultant/Half-Like, Ke (Elimination Rate)—Half-Life, Oct. 14, 2002.

Encyclopedia Britannica Online, Types of Drugs>Antimicrobial Drugs>Antibiotics>Macrolides, 2006.

Excenel, Swine Health Management, Prewean Program. Pfizer Salud Animal, 2005.

Fabrication of Metronidazole Strips, 996 Die Pharmazie 50(Feb. 1995) No. 2.

Five vs. 10 Days of Therapy for *Streptococcal pharyngitis*, American Family Physician, Feb. 15, 2001.

Food and Drug Administration Center for Drug Evaluation and Research Approved Drug Products With Therapetutic Equivalence Evaluations, 24th Edition, 2004.

Highlights on Antineoplastic Drugs, Pharmacia, vol. 11. No. 4, 1993.

Jock Itch and Other dermatophytes . . . , Mycolog, 2002.

Klarithran, Ranbaxy(SA)(PTY) LTD, Jun. 2005.

MedicineNet.com, Generic Name: Acyclovir, Brand Name: Zovirax, Dec. 31, 1997.

Meeting the Challenge of a New Generation of Respiratory Pathogens, MAC. (1999).

The Merck Index, An Encyclopedia of Chemicals, Drugs, and Biologicals, Twelfth Edition, pp. 397-398. (1996).

Methods of Formulating Controlled Release Products Outside of the Claims of Forest Laboratory Patents U.S. 4,369,172 and U.S. 4,389,393, Technical Information, Dow Chemical, Feb. 1991.

Miconazole, The Merck Index Results-Form View, Monograph No. 06202, 2001.

Mode of Action of Macrolides in Blocking Translation During Bacterial Protein Synthesis: Blocking Peptidyltransferase. Doc Kaiser's Microbiology Home Page, Oct. 13, 2004.

Module 8—Therapeutics. May 25, 2002, Newcastle., BPAIIG Immunology/Infectious Diseases Training Programme, Module: Therapeutics.

Neisseria Meningitidis, The Doctor's Doctor, Nov. 8, 2004.

New-Generation Aromatase Inhibitor for Breast Cancer: Anastrozole Challenges Tamoxifen in First-Line Therapy, 10th European Cancer Conference (ECCO 10), Vienna, Austria/ Sep. 12-16, 1999.

New Product Newswire, Drug Topics Archive, Aug. 5, 2002.

Nitrofurantoin, Eckerd Prescription Advisor, Feb. 15, 2001.

Nursing, Cancer Nursing: Principles and Practice, Fifth Edition, Jones and Bartlett Publishers, 2000.

Oral Capecitabine Should Improve Convenience of Chemoradiation for Locally Advanced Rectal Cancer-New Treatment Appears to be Safe and Effective, PeerView Press, Chemotherapy (ICAAC), Sep. 27-30, 2002; San Diego, CA., 40th Annual Meeting of Infectious Diseases Society.

Pharmaceuticals, Pharmacos Unit F2 Pharmaceuticals V 6.0, Eudralex Collection 3AQ19a 1992.

Physicians Desk Reference, PDR 57 Edition 2003, p. 402/Abbott.

Procardia XL (Nifedipine) Extended Release Tablets For Oral Use, 69-4467-00-8, Pfizer Labs, Aug. 2003.

Summary of Product Characteristics, Doxycycline Capsules BP 50 mg, Apr. 1997.

Sustained or Differential Release Type, USPTO Classification Definitions (Dec. 2002 Edition) 964.

Testicular Cancer: Questions and Answers, Cancer Facts, National Cancer Institute, Aug. 14, 2003.

Traditional Chemotherapy, Chapter 25 from Prevention and Therapy of Cancer and Other Common Disease: Alternative and Traditional Approaches; Infomedix 1996.

ANTIBIOTIC COMPOSITION WITH INHIBITOR

This application is a continuation of U.S. application Ser. No. 09/791,536, filed Feb. 23, 2001, now U.S. Pat. No. 6,565,882 which claims the priority of United States Provisional Application No. 60/184,582, filed on Feb. 24, 2000.

This invention relates to antibiotics that contain beta-lactam rings that are subject to attack by beta-lactamases in combination with beta-lactamase inhibitors.

Antibiotics with beta-lactam rings, for example, pencillins and cephalosporins, are susceptible to attack from the beta-lactamases (sometimes called penicillinases) that will chemically inactivate the antibiotic. Clavulanic acid, and its derivatives, as well as sulbactam are generally used to bind irreversibly to the beta-lactamase to prevent its activity against such an antibiotic. Typically, there is provided an antibiotic composition that includes the inhibitor with such combinations generally being delivered as an immediate release dosage form.

The present invention relates to an improved antibiotic composition that is comprised of at least four different dosage forms, two of which include at least one antibiotic with a beta-lactam ring (or any portions of such a ring) and two of which include at least one beta-lactamase inhibitor, with the four different dosage forms having release profiles such that there is a first dosage form that releases said at least one antibiotic, a second dosage form that releases at least one beta-lactamase inhibitor, a third dosage form that releases said at least one antibiotic, and a fourth dosage form that releases said at least one inhibitor, with the release profile of the first and second dosage forms being such that the maximum serum concentration of the inhibitor is reached at a time no sooner and preferably after the time at which the maximum serum concentration of the antibiotic released from the first dosage form is achieved, with the third dosage form having a release profile such that the second antibiotic achieves a maximum serum concentration at a time no sooner than and preferably after the time at which the inhibitor released from the second dosage form reaches a maximum serum concentration, and with the fourth dosage form having a release profile such that the maximum serum concentration of the inhibitor released from the fourth dosage form is achieved at a time no sooner and preferably after a time that the maximum serum concentration is reached for the at least one antibiotic released from the third dosage form.

In one preferred embodiment, the initiation of release from the second, third and fourth dosage form occurs at least one hour after initiation of release from the first, second and third form, respectively.

In a preferred embodiment of the present invention, a maximum serum concentration for the antibiotic released from the first dosage form is achieved in no more than about three hours; the maximum serum concentration for the inhibitor released from the second dosage form is reached in a time of from about three to six hours; the maximum serum concentration of the antibiotic released from the third dosage form is reached in from about six to nine hours, and the maximum serum concentration released from the fourth dosage form is achieved in no more than twelve hours, with such times being measured from the time of administration of the antibiotic composition that is comprised of the at least four different dosage forms.

In a preferred embodiment of the present invention, the at least four dosage forms are provided with release profiles such that the inhibitor is released from the second dosage form after the maximum serum concentration is achieved for antibiotic released from the first dosage form; antibiotic is released from the third dosage form after the maximum serum concentration is reached for the inhibitor released from the second dosage form, and inhibitor is released from the fourth dosage form after the maximum serum concentration is reached for the antibiotic released from the third dosage form.

It is to be understood that when it is disclosed herein that a dosage form initiates release after another dosage form, such terminology means that the dosage form is designed and is intended to produce such later initiated release. It is known in the art, however, notwithstanding such design and intent, some "leakage" of antibiotic or inhibitor may occur. Such "leakage" is not "release" as used herein.

Although, in a preferred embodiment there are four dosage forms, it is possible to have more than four dosage forms, provided that there is successive alternate release of antibiotic and inhibitor, and each inhibitor release achieves a serum concentration maximum no sooner than and preferably after the serum concentration maximum of the immediately preceding antibiotic released, and the next antibiotic released reaches a serum concentration maximum no sooner than and preferably after the serum concentration maximum is achieved for the immediately preceding inhibitor dosage form.

In an embodiment of the present invention each of the dosage forms that contains an inhibitor includes such inhibitor in an amount that is effective to inhibit chemical inactivation of the antibiotic by beta-lactamase. In general, the dosage forms that contain the inhibitor contain such an inhibitor in an amount from about 20 percent to about 80 percent.

Similarly, the dosage forms that contain the antibiotic generally include the antibiotic in an amount from about 30 percent to about 80 percent. Each of the dosage forms that deliver antibiotics include from 30% to 70% of the dosage of the antibiotic to be delivered by the composition.

In accordance with a preferred embodiment, the first dosage form that releases antibiotic is an immediate release dosage form. The second, third, and fourth dosage forms are delayed release dosage forms, which may be pH independent or pH dependent (enteric) dosage forms. The second, third and fourth dosage forms are formulated in a matter to provide the release profiles as hereinabove described.

At least four different dosage forms can be formulated into the overall antibiotic composition of the present invention, by procedures generally known in the art. For example, each of the dosage forms may be in the form of a pellet or a particle, with pellet particles being formed into the overall composition, in the form, for example, of the pellet particles in a capsule, or the pellet particles embedded in a tablet or suspended in a liquid suspension.

The antibiotic composition of the prevent invention may be administered, for example, by any of the following routes of administration: sublingual, transmucosal, transdermal, parenteral, and preferably are administered orally. The composition includes a therapeutically effective amount of the antibiotic, which amount will vary with the antibiotic to be used, the disease or infection to be treated, and the number of times that the composition is to be delivered in a day.

The antibiotic product of the present invention, as hereinabove described, may be formulated for administration by a variety of routes of administration. For example, the antibiotic product may be formulated in a way that is suitable for topical administration; administration in the eye or the ear; rectal or vaginal administration; as nose drops; by inhalation; as an injectable; or for oral administration. In a preferred embodiment, the antibiotic product is formulated in a manner such that it is suitable for oral administration.

For example, in formulating the antibiotic product for topical administration, such as by application to the skin, the antibiotic may be formulated for topical administration by including such dosage forms in an oil-in-water emulsion, or a water-in-oil emulsion. In such a formulation, the immediate release dosage forms are in the continuous phase, and the delayed release dosage form is in a discontinuous phase. For example, there may be provided an oil-in-water-in-oil-in-water emulsion, with oil being a continuous phase that contains the immediate release component, water dispersed in the oil containing a first delayed release dosage form, and oil dispersed in the water containing a second delayed release dosage form, and water dispersed in the oil containing a third delayed release dosage form.

It is also within the scope of the invention to provide an antibiotic product in the form of a patch, which includes different antibiotic and inhibitor dosage forms having different release profiles, as hereinabove described.

Furthermore, the antibiotic product with different dosage forms with different release profiles may be formulated for rectal or vaginal administration, as known in the art. This may take the form of a cream or emulsion, or other dissolvable dosage forms similar to those used for topical administration.

As a further embodiment, the antibiotic product may be formulated for use in inhalation therapy by coating the particles and micronizing the particles for inhalation.

In a preferred embodiment, the antibiotic product is formulated in a manner suitable for oral administration. Thus, for example, for oral administration, each of the dosage forms may be used as a pellet or a particle, with a pellet or particle then being formed into a unitary pharmaceutical product, for example, in a capsule, or embedded in a tablet, or suspended in a liquid for oral administration.

Alternatively, in formulating an oral delivery system, each of the dosage forms of the product may be formulated as a tablet, with each of the tablets being put into a capsule to produce a unitary antibiotic product. Thus, for example, antibiotic products may include a first dosage form in the form of a tablet that is an immediate release tablet, and may also include three additional tablets, each of which provides for a delayed release of the antibiotic and inhibitor, as hereinabove described.

As hereinabove described, the antibiotics that are employed in the present invention are ones that include a beta-lactam ring or a portion thereof such as for example, penicillin derivatives, such as penicillin V, penicillin G, penicillin, ampicillin, amoxicillin, carbenicillin, ticarcillin, piperacillin, nafcillin, cloxacillin, dicloxacillin, monobactams such as aztreonam, carbapenems such as imipenem, cephalosporins such as cefoxitan, cephalexin, ceferiaxone, cefuroxime, cefpodoxime, and others.

The beta-lactamase inhibitors maybe any one of a wide variety that are effective to inhibit the action of beta-lactamases on a beta-lactam ring, such as clavulanic acid and its derivatives, sulbactam.

In one embodiment, the product contains sufficient antibiotic for a twenty-four hour period whereby the product is administered once a day.

The Immediate Release Component

The immediate release portion of this system can be a mixture of ingredients that breaks down quickly after administration to release the antibiotic. This can take the form of either a discrete pellet or granule that is mixed in with, or compressed with, the other three components.

The materials to be added to the antibiotics for the immediate release component can be, but are not limited to, microcrystalline cellulose, corn starch, pregelatinized starch, potato starch, rice starch, sodium carboxymethyl starch, hydroxypropylcellulose, hydroxypropylmethylcellulose, hydroxyethylcellulose, ethylcellulose, chitosan, hydroxychitosan, hydroxymethylatedchitosan, cross-linked chitosan, cross-linked hydroxymethyl chitosan, maltodextrin, mannitol, sorbitol, dextrose, maltose, fructose, glucose, levulose, sucrose, polyvinylpyrrolidone (PVP), acrylic acid derivatives (Carbopol, Eudragit, etc.), polyethylene glycols, such a low molecular weight PEGs (PEG2000–10000) and high molecular weight PEGs (Polyox) with molecular weights above 20,000 daltons.

It may be useful to have these materials present in the range of 1.0 to 60% (W/W).

In addition, it may be useful to have other ingredients in this system to aid in the dissolution of the drug, or the breakdown of the component after ingestion or administration. These ingredients can be surfactants, such as sodium lauryl sulfate, sodium monoglycerate, sorbitan monooleate, polyoxyethylene sorbitan monooleate, glyceryl monostearate, glyceryl monooleate, glyceryl monobutyrate, one of the non-ionic surfactants such as the Pluronic line of surfactants, or any other material with surface active properties, or any combination of the above.

These materials may be present in the rate of 0.05–15% (W/W).

The Delayed Release Component

The components in this composition are the same immediate release unit, but with additional polymers integrated into the composition, or as coatings over the pellet or granule.

Materials that can be used to obtain a delay in release suitable for this component of the invention can be, but are not limited to, polyethylene glycol (PEG) with molecular weight above 4,000 daltons (Carbowax, Polyox), waxes such as white wax or bees wax, paraffin, acrylic acid derivatives (Eudragit), propylene glycol, and ethylcellulose.

Typically these materials can be present in the range of 0.5–25% (W/W) of this component.

The Enteric Release Component

The components in this composition are the same as the immediate release component, but with additional polymers integrated into the composition, or as coatings over the pellet or granule.

The kind of materials useful for this purpose can be, but are not limited to, cellulose acetate pthalate, Eudragit L, and other pthalate salts of cellulose derivatives.

These materials can be present in concentrations from 4–20% (W/W).

The present invention will be described with respect to the following examples; however, the scope of the invention is not to be limited thereby. Unless otherwise stated, all parts and percentages set forth in this specification are by weight.

EXAMPLES

| | Ingredient | Conc. (% W/W) |
|---|---|---|
| | Immediate Release Component | |
| Example 1: | Amoxicillin | 65% (W/W) |
| | Microcrystalline cellulose | 20 |
| | Povidone | 10 |
| | Croscarmellose sodium | 5 |
| Example 2: | Amoxicillin | 55% (W/W) |
| | Microcrystalline cellulose | 25 |
| | Povidone | 10 |
| | Croscarmellose sodium | 10 |
| Example 3: | Amoxicillin | 75% (W/W) |
| | Polyethylene glycol 4000 | 10 |
| | Polyethylene glycol 2000 | 10 |
| | Hydroxpropylcellulose | 5 |
| Example 4: | Amoxicillin | 75% (W/W) |
| | Polyethylene glycol 8000 | 20 |
| | Polyvinylpyrrolidone | 5 |
| Example 5: | Clarithromycin | 65% (W/W) |
| | Microcrystalline cellulose | 20 |
| | Hydroxyproplycellulose | 10 |
| | Croscarmellose sodium | 5 |
| Example 6: | Clarithromycin | 75% (W/W) |
| | Microcrystalline cellulose | 15 |
| | Hydroxyproplycellulose | 5 |
| | Croscarmellose sodium | 5 |
| Example 7: | Clarithromycin | 75% (W/W) |
| | Polyethylene glycol 4000 | 10 |
| | Polyethylene glycol 2000 | 10 |
| | Hydroxypropylcellulose | 5 |
| Example 8: | Clarithromycin | 75% (W/W) |
| | Polyethylene glycol 8000 | 20 |
| | Polyvinylpyrrolidone | 5 |
| Example 9: | Ciprofoxacin | 65% (W/W) |
| | Microcrystalline cellulose | 15 |
| | Hydroxypropylcellulose | 5 |
| | Croscarmellose sodium | 5 |
| Example 10: | Ciprofoxacin | 75% (W/W) |
| | Microcrystalline cellulose | 15 |
| | Hydroxypropylcellulose | 5 |
| | Croscarmellose sodium | 5 |
| | Delayed Release Component | |
| Example 11: | Ciprofoxacin | 75% (W/W) |
| | Polyethylene glycol 4000 | 10 |
| | Polyethylene glycol 2000 | 10 |
| | Hydroxypropylcellulose | 5 |
| Example 12: | Ciprofoxacin | 75% (W/W) |
| | Polyethylene glycol 8000 | 20 |
| | Polyvinylpyrrolidone | 5 |
| Example 13: | Ceftibuten | 75% (W/W) |
| | Polyethylene glycol 4000 | 10 |
| | Polyethylene glycol 2000 | 10 |
| | Hydroxpropylcellulose | 5 |
| Example 14: | Ceftibuten | 75% (W/W) |
| | Polyethylene glycol 4000 | 20 |
| | Polyvinylpyrrolidone | 5 |
| Example 15: | Amoxicillin | 65% (W/W) |
| | Microcrystalline cellulose | 20 |
| | Cellulose Acetate Pthalate | 15 |
| Example 16: | Amoxicillin | 55% (W/W) |
| | Microcrystalline cellulose | 25 |
| | Cellulose Acetate Pthalate | 10 |
| | Hydroxyproplmethylcellulose | 10 |
| Example 17: | Amoxicillin | 65% (W/W) |
| | Polyox | 20 |
| | Hydroxypropylcellulose pthalate | 10 |
| | Eudragit E 30D | 5 |
| Example 18: | Amoxicillin | 40% (W/W) |
| | Microcrystalline Cellulose | 40 |
| | Cellulose Acetate Pthalate | 10 |
| Example 19: | Clarithromycin | 70% (W/W) |
| | Hydroxypropylcellulose pthalate | 15 |
| | Croscarmellose sodium | 10 |
| Example 20: | Clarithromycin | 75% (W/W) |
| | Polyethylene glycol 2000 | 10 |
| | Eudragit E 30D | 15 |
| Example 21: | Clarithromycin | 40% (W/W) |
| | Lactose | 50 |
| | Eudragit E 30D | 10 |
| Example 22: | Ciprofoxacin | 65% (W/W) |
| | Microcrystalline Cellulose | 20 |
| | Eudragit E 30D | 10 |
| Example 23 | Ciprofoxacin | 75% (W/W) |
| | Microcrystalline Cellulose | 15 |
| | Hydroxypropycellulose pthalate | 10 |
| Example 24 | Ciprofoxacin | 80% (W/W) |
| | Lactose | 10 |
| | Eudragit E 30D | 10 |
| Example 25 | Ciprofoxacin | 70% (W/W) |
| | Polyethylene glycol 4000 | 20 |
| | Cellulose acetate pthalate | 10 |
| Example 26 | Ceftibuten | 60% (W/W) |
| | Polyethylene Glycol 2000 | 10 |
| | Lactose | 20 |
| | Eudragit E 30D | 10 |
| Example 27 | Ceftibuten | 70% (W/W) |
| | Microcrystalline Cellulose | 20 |
| | Cellulose acetate pthalate | 10 |
| Example 28: | Clavulanate potassium | 65% (W/W) |
| | Microcyrstalline cellulose | 20 |
| | Cellulose Acetate Pthalate | 15 |
| Example 29: | Clavulanate potassium | 55% (W/W) |
| | Microcrystalline cellulose | 25 |
| | Cellulose Acetate Pthalate | 10 |
| | Hydroxypropylmethlycellulose | 10 |
| Example 30: | Clavulanate potassium | 65% (W/W) |
| | Polyox | 20 |
| | Hydroxypropylcellulose pthalate | 10 |
| | Eudragit E 30D | 5 |
| Example 31 | Clavulanate potassium | 40% (W/W) |
| | Microcrystalline cellulose | 40 |
| | Cellulose Acetate Pthalate | 10 |
| Example 32: | Clavulanate potassium | 70% (W/W) |
| | Hydroxypropylcellulose pthalate | 15 |
| | Croscarmellose sodium | 10 |
| Example 33: | Clavulanate potassium | 75% (W/W) |
| | Polyethylene glycol 2000 | 10 |
| | Eudragit E 30D | 15 |
| Example 34: | Clavulanate potassium | 40% (W/W) |
| | Lactose | 50 |
| | Eudragit E 30D | 10 |
| Example 35: | Clavulanate potassium | 65% (W/W) |
| | Microcrystalline Cellulose | 20 |
| | Eudragit E 30D | 10 |
| Example 36: | Sulbactam | 75% (W/W) |
| | Microcrystalline cellulose | 15 |
| | Hydroxyropylcellulose pthalate | 10 |
| Example 37: | Sulbactam | 80% (W/W) |
| | Lactose | 10 |
| | Eudragit E 30D | 10 |
| Example 38: | Sulbactam | 70% (W/W) |
| | Polyethylene glycol 4000 | 20 |
| | Cellulose acetate pthalate | 10 |
| Example 39: | Sulbactam | 60% (W/W) |
| | Polyethylene glycol 2000 | 10 |
| | Lactose | 20 |
| | Eudragit E 30D | 10 |
| Example 40: | Sulbactam | 70% (W/W) |
| | Microcrystalline cellulose | 20 |
| | Cellulose Acetate pthalate | 10 |
| Example 41: | Clavulanate potassium | 65% (W/W) |
| | Microcrystalline cellulose | 20 |
| | Polyox | 10 |
| | Croscarmellose Sodium | 5 |
| Example 42: | Clavulanate potassium | 55% (W/W) |
| | Microcrystalline cellulose | 25 |
| | Polyox | 10 |
| | Glyceryl monooleate | 10 |

-continued

| | Ingredient | Conc. (% W/W) |
|---|---|---|
| Example 43: | Clavulanate potassium | 65% (W/W) |
| | Polyox | 20 |
| | Hydroxyproplcellulose | 10 |
| | Croscarmellose sodium | 5 |
| Example 44: | Clavulanate potassium | 70% (W/W) |
| | Polyox | 20 |
| | Hydroxypropycellulose | 5 |
| | Croscarmellose sodium | 5 |

Example 45.

1 Beta Lactam Antibiotic and Beta-Lactamase Inhibitor Matrix Pellet Formulation and Preparation Procedure 45.1 Pellet Formulation The composition of the antibiotic or inhibitor matrix pellets provided in Table 1.

TABLE 1

Composition of Antibiotic Pellets

| Component | Percentage (%) |
|---|---|
| Antibiotic or Inhibitor | 50 |
| Avicel PH 101 | 20 |
| Lactose | 20 |
| PVP K29/32* | 10 |
| Purified Water | |
| Total | 100 |

*PVP K29/32 was added as a 20% w/w aqueous solution during wet massing.

*PVP K29/32 was added as a 20% W/W aqueous solution during wet massing.

45.2 Preparation Procedure for Antibiotic or Inhibitor Matrix Pellets 45.2.1 Blend antibiotic or inhibitor and Avicel® PH 101 using a Robot Coupe high shear granulator.

45.2.2 Add 20% Povidone K29/32 binder solution slowly into the powder blend under continuous mixing.

45.2.3 Extrude the wet mass using an LCI Bench Top Granulator. The diameter of the screen of the Bench Top Granulator was 1.0 mm.

45.2.4 Spheronize the extrudate using a Model SPH20 Caleva Spheronizer.

45.2.5 Dry the spheronized pellets at 50° C. overnight.

45.2.6 Pellets between 16 and 30 Mesh were collected for further processing.

45.2.7 The above procedure is used to prepare pellets that contain an antibiotic and pellets that contain an inhibitor.

45.3 Preparation of an Eudragit® L 30 D-55 Aqueous Coating Dispersion 45.3.1 Dispersion Formulation The composition of the aqueous Eudragit L30D-55 dispersion applied to the antibiotic matrix pellets and to the inhibitor matrix pellets is provided below in Table 2.

TABLE 2

Eudragit ® L 30 D-55 Aqueous Coating Dispersion

| Component | Percentage (%) |
|---|---|
| Eudragit ® L 30 D-55 | 55.0 |
| Triethyl Citrate | 1.6 |
| Talc | 8.0 |
| Purified Water | 37.4 |
| Solids Content | 25.5 |
| Polymer Content | 15.9 |

45.4 Preparation Procedure for an Eudragit® L 30 D-55 Aqueous Dispersion 45.4.1 Suspend triethyl citrate and talc in deionized water.

45.4.2 The TEC/talc suspension is then homogenized using a PowerGen 700 high shear mixer.

45.4.3 Add the TEC/talc suspension slowly to the Eudragit® L 30 D-55 latex dispersion while stirring.

45.4.4 Allow the coating dispersion to stir for one hour prior to application onto the antibiotic matrix pellets.

45.5 Preparation of an Eudragit® S 100 Aqueous Coating Dispersion 45.5.1 Dispersion Formulation The composition of the aqueous Eudragit® S 100 dispersion applied to the inhibitor matrix pellets is provided below in Table 3.

TABLE 3

Eudragit ® S 100 Aqueous Coating Dispersion

| Component | Percentage (%) |
|---|---|
| Part A | |
| Eudragit ® S 100 | 12.0 |
| 1 N Ammonium Hydroxide | 6.1 |
| Triethyl Citrate | 6.0 |
| Purified Water | 65.9 |
| Part B | |
| Talc | 2.0 |
| Purified Water | 8.0 |
| Solid Content | 20.0 |
| Polymer Content | 12.0 |

45.6 Preparation Procedure for an Eudragit® S 100 Aqueous Dispersion

Part A:

45.6.1 Dispense Eudragit® S 100 powder in deionized water with stirring.

45.6.2 Add ammonium hydroxide solution drop-wise into the dispersion with stirring.

45.6.3 Allow the partially neutralized dispersion to stir for 60 minutes.

45.6.4 Add triethyl citrate drop-wise into the dispersion with stirring. Stir for about 2 hours prior to the addition of Part B.

Part B:

45.6.5 Disperse talc in the required amount of water 45.6.6 Homogenize the dispersion using a PowerGen 700D high shear mixer.

45.6.7 Part B is then added slowly to the polymer dispersion in Part A with a mild stirring.

45.7 Coating Conditions for the Application of Aqueous Coating Dispersions

The following coating parameters are used for coating with each of the Eudragit® L 30 D-55 and Eudragit® S 100 aqueous film coatings.

| | |
|---|---|
| Coating Equipment | STREA 1 ™ Table Top Laboratory Fluid Bed Coater |
| Spray nozzle diameter | 1.0 mm |
| Material Charge | 300 gram |
| Inlet Air Temperature | 40 to 45° C. |
| Outlet Air Temperature | 30 to 33° C. |
| Atomization Air Pressure | 1.8 Bar |
| Pump Rate | 2 gram per minute |

45.7.1 Coat matrix pellets with L30 D-55 dispersion such that you apply 12% coat weight gain to the pellets.

45.7.2 Coat matrix pellets with L30 D-55 dispersion such that you apply 30% coat weight gain to the pellets.

45.7.3 Coat matrix pellets with S100 dispersion such that you apply 20% coat weight gain to the pellets.

45.8 Encapsulation of the Antibiotic and Inhibitor Pellets

Pellets are filled into size 00 hard gelatin capsules at a ratio of 20%: 30%: 20%: 30% Immediate-release matrix pellets (uncoated), L30 D-55 coated pellets 12% weight gain, L30D-55 coated pellets 30% weight gain and S100 coated pellets respectively. The capsule is filled with the four different pellets to achieve the desired dosage.

The immediate release pellets contain the antibiotic; the L30 D-55 12% weight gain coated pellets contain the inhibitor; the L30 D-55 30% weight gain coated pellets contain the antibiotic and the S100 coated pellets contain the inhibitor.

The present invention is advantageous in that the beta-lactamase inhibitor will be dosed at a lower peak concentration, giving rise to fewer side effects. The alternative dosing of the antibiotic and the inhibitor will alternate the exposure to the bacteria in such a way as to make the antibiotic more effective than if they were co-administered, and thereby competing with each other for sites on the bacterial cell wall receptors.

Numerous modifications and variations of the present invention are possible in light of the above teachings, therefore, within the scope of the appended claims, the invention may be practiced otherwise than as particularly described.

What is claimed is:

1. A once-a-day antibiotic composition comprising:
a mixture of at least four dosage forms, two of said dosage forms each comprising at least one antibiotic with a beta-lactam ring or portion thereof and a pharmaceutically acceptable carrier; and two of said dosage forms each comprising at least one beta-lactamase inhibitor and a pharmaceutically acceptable carrier; each of said four dosage forms initiating release of said antibiotic or of said inhibitor at different times, whereby Cmax in serum for both the total amount of antibiotic and the total amount of inhibitor is acheived in no more than about twelve hours after administration, and said once-a-day antibiotic composition contains a therapeutically effective amount of said at least one antibiotic, said therapeutically effective amount being the total dosage of said at least one antibiotic for a twenty four hour period.

2. The antibiotic composition of claim 1 wherein the first dosage form is an immediate release dosage form and the second and third dosage forms are delayed release dosage forms.

3. The antibiotic composition of claim 2, wherein the first dosage form contains antibiotic, the second dosage form contains inhibitor, the third dosage form contains antibiotic, and the fourth dosage form contains inhibitor.

4. The antibiotic composition of claim 3 wherein the inhibitor is released from the second dosage form after the antibiotic released from the first dosage form reaches maximum serum concentration, the antibiotic is released from the third dosage form after the inhibitor released from the second dosage form reaches maximum serum concentration and inhibitor is released from the fourth dosage form after antibiotic released from the third dosage form reaches maximum serum concentration.

5. The antibiotic composition of claim 1 wherein the antibiotic composition is an oral dosage form.

6. The antibiotic composition of claim 3 wherein the second dosage form initiates release of inhibitor at least one hour after initiation of release of antibiotic from the first dosage form, the third dosage form initiates release of antibiotic at least one hour after initiation of release of inhibitor from the second dosage form and the fourth dosage form initiates release of inhibitor at least one hour after initiation of release of antibiotic from the third dosage form.

7. The antibiotic composition of claim 3 wherein the first dosage form includes from 30% to 80% of the antibiotic delivered by the composition and the remainder of the antibiotic is delivered by the third dosage form.

8. The antibiotic composition of claim 3, wherein the antibiotic released from the first dosage form reaches a maximum serum concentration in no more than about three hours after administration; wherein the inhibitor released from the second dosage form reaches a maximum serum concentration in about three to six hours after administration; wherein the antibiotic released from the third dosage form reaches a maximum serum concentration in from about six to nine hours after administration; and wherein the inhibitor released from the fourth dosage form reaches a maximum serum concentration in no more than twelve hours after administration.

9. The antibiotic composition of claim 3, wherein the inhibitor released from the second dosage form reaches a maximum serum concentration after the antibiotic released from the first dosage form reaches a maximum serum concentration; the antibiotic released from the third dosage form reaches a maximum serum concentration after the inhibitor released from the second dosage form reaches a maximum serum concentration; and the inhibitor released from the fourth dosage form reaches a maximum serum concentration after the antibiotic released from the third dosage form reaches a maximum serum concentration.

10. The antibiotic composition of claim 3, wherein the antibiotic released from the first dosage form reaches a maximum serum concentration in no more than about three hours after administration; wherein the inhibitor released from the second dosage form reaches a maximum serum concentration in about three to six hours after administration; wherein the antibiotic released from the third dosage form reaches a maximum serum concentration in from about six to nine hours after administration; and wherein the inhibitor released from the fourth dosage form reaches a maximum serum concentration in no more than twelve hours after administration.

11. A process for treating a patient for a bacterial infection comprising treating the patient by administration of the antibiotic composition of claim 1, once-a-day.

12. A process for treating a patient for a bacterial infection comprising treating the patient by administration of the antibiotic composition of claim 2, once-a-day.

13. A process for treating a patient for a bacterial infection comprising treating the patient by administration of the antibiotic composition of claim 3, once-a-day.

14. A process for treating a patient for a bacterial infection comprising treating the patient by administration of the antibiotic composition of claim 4, once-a-day.

15. A process for treating a patient for a bacterial infection comprising treating the patient by administration of the antibiotic composition of claim 5, once-a-day.

16. A process for treating a patient for a bacterial infection comprising treating the patient by administration of the antibiotic composition of claim 6, once-a-day.

17. A process for treating a patient for a bacterial infection comprising treating the patient by administration of the antibiotic composition of claim 7, once-a-day.

18. A process for treating a patient for a bacterial infection comprising treating the patient by administration of the antibiotic composition of claim 8, once-a-day.

19. A process for treating a patient for a bacterial infection comprising treating the patient by administration of the antibiotic composition of claim 9, once-a-day.

20. A process for treating a patient for a bacterial infection comprising treating the patient by administration of the antibiotic composition of claim 10, once-a-day.

21. The composition of claim 1, wherein said at least one antibiotic with a beta-lactam ring or portion thereof is amoxicillin.

22. The composition of claim 1, wherein said at least one antibiotic with a beta-lactam ring or portion thereof is carbenicillin.

23. The composition of claim 1, wherein said beta-lactamase inhibitor is clavulanate or a derivative thereof.

24. The composition of claim 23, wherein said clavulanate or a derivative thereof is in the form of a salt.

25. The composition of claim 24, wherein said salt is clavulanate potassium.

26. The composition of claim 1, wherein said beta-lactamase inhibitor is sulbactam.

27. The antibiotic composition of claim 25, wherein the first antibiotic dosage form is an immediate release dosage form.

28. The composition of claim 1, wherein each of said antibiotic dosage forms is a delayed release dosage form.

29. The composition of claim 1, wherein each dosage form that contains said antibiotic is free of said beta-lactamase inhibitor and each dosage form that contains said beta-lactamase inhibitor is free of said antibiotic.

30. A process for treating a patient for a bacterial infection comprising treating the patient by administration of the antibiotic composition of claim 21, once-a-day.

31. A process for treating a patient for a bacterial infection comprising treating the patient by administration of the antibiotic composition of claim 22, once-a-day.

32. A process for treating a patient for a bacterial infection comprising treating the patient by administration of the antibiotic composition of claim 23, once-a-day.

33. A process for treating a patient for a bacterial infection comprising treating the patient by administration of the antibiotic composition of claim 24, once-a-day.

34. A process for treating a patient for a bacterial infection comprising treating the patient by administration of the antibiotic composition of claim 25, once-a-day.

35. A process for treating a patient for a bacterial infection comprising treating the patient by administration of the antibiotic composition of claim 26, once-a-day.

36. A process for treating a patient for a bacterial infection comprising treating the patient by administration of the antibiotic composition of claim 27, once-a-day.

37. A process for treating a patient for a bacterial infection comprising treating the patient by administration of the antibiotic composition of claim 28, once-a-day.

38. A process for treating a patient for a bacterial infection comprising treating the patient by administration of the antibiotic composition of claim 29, once-a-day.

* * * * *